United States Patent
Sanghvi (10) Patent No.: US 10,765,837 B2
(45) Date of Patent: Sep. 8, 2020

(54) METHOD AND DEVICE FOR SHEATHLESS ARTERIAL CATHETERIZATION

(71) Applicant: Cordis Corporation, Fremont, CA (US)

(72) Inventor: Kintur A. Sanghvi, Princeton Junction, NJ (US)

(73) Assignee: Cardinal Health Switzerland 515 GMBH, Bar Zug (CH)

( * ) Notice: Subject to any disclaimer, the term of this patent is extended or adjusted under 35 U.S.C. 154(b) by 0 days.

(21) Appl. No.: 14/868,988

(22) Filed: Sep. 29, 2015

(65) Prior Publication Data

US 2016/0089516 A1 Mar. 31, 2016

Related U.S. Application Data

(60) Provisional application No. 62/057,764, filed on Sep. 30, 2014.

(51) Int. Cl.
| | | |
|---|---|---|
| *A61M 29/00* | (2006.01) | |
| *A61M 25/09* | (2006.01) | |
| *A61M 29/02* | (2006.01) | |
| *A61M 25/01* | (2006.01) | |

(52) U.S. Cl.
CPC ...... *A61M 25/09041* (2013.01); *A61M 29/00* (2013.01); *A61M 29/02* (2013.01); *A61M 2025/0183* (2013.01)

(58) Field of Classification Search
CPC ............ A61M 25/09041; A61M 29/00; A61M 29/02; A61M 2025/0183
USPC .................................. 604/507, 104, 103.04
See application file for complete search history.

(56) References Cited

U.S. PATENT DOCUMENTS

| | | |
|---|---|---|
| 5,492,530 A | 2/1996 | Fischell et al. |
| 5,496,344 A | 3/1996 | Kanesaka et al. |
| 8,206,320 B2 | 6/2012 | Deal et al. |
| 8,747,428 B2 | 6/2014 | Fischell et al. |
| 9,119,935 B2 | 9/2015 | Fischell et al. |
| 9,399,118 B2 | 7/2016 | Kume et al. |
| 2003/0163117 A1* | 8/2003 | Ishii ................. A61M 25/0021 604/523 |

(Continued)

FOREIGN PATENT DOCUMENTS

| | | |
|---|---|---|
| CN | 202052191 U | 11/2011 |
| WO | 13/106511 A1 | 7/2013 |

OTHER PUBLICATIONS

Tariq Ashraf, Ziauddin Panhwar, Sultana Habib, Muhammad Anis Merron, Fahad Shamsi, Javed Arif, Size of radial and ulnar artery in local population. J Pak Med Assoc, pp. 817-819. vol. 60, No. 10, Oct. 2010. (Year: 2010).*

(Continued)

*Primary Examiner* — Amber R Stiles
(74) *Attorney, Agent, or Firm* — Arent Fox LLP (57) ABSTRACT

A dilator for sheathless access to a vessel of a patient, having a distal portion with a maximal outer diameter that extends from a distal end to a guidewire exit port and a proximal portion with a reduced profile that extends from the guidewire exit port to the proximal end and a lumen that extends between the distal end and the guidewire exit port. A first guidewire may be positioned within the vessel and the dilator advanced over the guidewire. A guide catheter may then be advanced over the dilator.

20 Claims, 12 Drawing Sheets (56) References Cited

U.S. PATENT DOCUMENTS

| | | | |
|---|---|---|---|
| 2005/0143770 A1* | 6/2005 | Carter | A61B 1/018 606/170 |
| 2006/0030876 A1* | 2/2006 | Peacock, III | A61F 2/013 606/200 |
| 2006/0217664 A1 | 9/2006 | Hattler et al. | |
| 2006/0247672 A1* | 11/2006 | Vidlund | A61B 17/3421 606/190 |
| 2006/0264906 A1* | 11/2006 | Pal | A61M 25/0009 604/523 |
| 2007/0083252 A1* | 4/2007 | McDonald | A61F 2/95 623/1.11 |
| 2007/0191810 A1* | 8/2007 | Kennedy | A61M 25/00 604/508 |
| 2008/0228169 A1* | 9/2008 | Schatz | A61M 25/00 604/528 |
| 2009/0088790 A1* | 4/2009 | Parodi | A61F 2/013 606/200 |
| 2013/0184735 A1* | 7/2013 | Fischell | A61M 29/00 606/191 |
| 2013/0281850 A1 | 10/2013 | Okajima et al. | |
| 2013/0317438 A1 | 11/2013 | Ellingwood et al. | |
| 2014/0052097 A1* | 2/2014 | Petersen | A61M 25/01 604/506 |
| 2014/0107681 A1 | 4/2014 | Davies et al. | |
| 2015/0057697 A1 | 2/2015 | Carlstrom et al. | |
| 2015/0066118 A1 | 3/2015 | O'Connell | |
| 2015/0133865 A1* | 5/2015 | Okamura | A61M 25/0662 604/164.1 |
| 2015/0360010 A1 | 12/2015 | Fischell et al. | |

OTHER PUBLICATIONS

International Preliminary Report on Patentability dated Apr. 4, 2017 in corresponding PCT/US2015/052866 application, 10 pages.
International Search Report and Written Opinion for PCT Application No. PCT/US2015/052866; dated Jan. 22, 2016.
Office Action dated Jul. 16, 2019 in connection with Chinese Patent Application No. 201580056525.X, 8 pages.
Examination Report No. 1 dated Aug. 23, 2019 in connection with Australian Patent Application No. 2015324033, 6 pages.
Search Report dated Jun. 28, 2019 in connection with Chinese Patent Application No. 201580056525.X, 2 pages.
Communication pursuant to Article 94(3) EPC dated Aug. 26, 2019 in connection with European Patent Application No. 15 782 136.4, 7 pages.

* cited by examiner

FIG. 13

METHOD AND DEVICE FOR SHEATHLESS ARTERIAL CATHETERIZATION

CROSS REFERENCE TO RELATED APPLICATIONS

This application claims priority from and benefit of U.S. Provisional Patent Application Ser. No. 62/057,764 filed Sep. 30, 2014, which is entitled "DEVICE TO ACHIEVE AND USE SHEATHLESS RADIAL ARTERY ACCESS FOR TRANSRADIAL CATHETERIZATION," which is assigned to the assignee hereof and is incorporated by reference in its entirety.

FIELD OF THE PRESENT DISCLOSURE

This disclosure relates to medical devices for percutaneous endovascular procedures and, more particularly, to techniques for transradial catheterization using radial artery access.

BACKGROUND

A growing number of interventional procedures may be performed percutaneously by using one or more catheters to access treatment areas in the patient's vasculature or other regions. Although many procedures typically gain access through the femoral artery, certain access related complications are associated with this entry point. For example, major bleeding complication, retroperitoneal bleeding, blood transfusion, pseudoaneursym, difficult to achieve hemostasis following the completion of the procedure, prolonged period of immobilization, are more likely to happen with transfemoral approach. Larger the entry hole in the femoral artery, more likely are the above-mentioned complications. Correspondingly, it may be desirable to catheterize other vessels to reduce or avoid such complications or catheterize the femoral artery with a smaller diameter entry hole.

One suitable technique for catheterization is to gain access through the radial artery located in the patient's wrist. Transradial catheterization offers a number of benefits compared to the femoral approach, including a reduction in bleeding complications and more rapid ambulation. However, certain challenges are associated catheterization of this small size vessel. For example, spasm, pain and/or discomfort may occur. Radial artery catheterization may also lead to iatrogenic radial artery occlusion. Still further, radial catheterization limits the overall diameter of the guide catheter being used may be limited to 6 French size in most patients, precluding the ability to perform some of the more complex coronary, peripheral endovascular and structural cardiac intervention procedures. The important predictors of radial artery spasm during transradial catheterization include a smaller size body mass index, smaller radial artery, and larger "sheath diameter to radial artery diameter index." As will be appreciated, spasm may lead to pain, irritation and inflammation, reducing the success rate of transradial catheterization. Likewise, the most important predictors of radial artery occlusion after transradial catheterization include the sex of the patient, as females typically exhibit relatively smaller vessel diameters, and the use of a 6 French (or larger) sheath. Therefore, all of these challenges result from the relatively smaller diameter of the radial artery and the corresponding increased potential for stretching, expanding or irritating the artery by inserting a device having an outer diameter larger than the inner diameter of the radial artery.

These challenges are exacerbated when a sheath is employed in the catheterization procedure. Since the guide catheter is delivered through the sheath, it necessarily must have a greater outside diameter. The outer diameter of a sheath is on average 0.60 millimeter larger than the corresponding size catheter. To address this situation, attempts have been made to develop sheathless systems. Some approaches nevertheless still require a radial sheath and thus are not true sheathless systems. Currently available sheathless systems are expensive and increase costs by requiring use of a new system with each guide catheter exchange. Currently available sheathless systems also require specific configurations of the guide catheter being used with the system, and correspondingly limit the choice of catheter size and shape, potentially preventing the operator from using a preferred guide catheter shape or design.

Accordingly there is a need for a device and method for transradial catheterization that allows the use of an increased diameter guide catheter by avoiding the necessity of deploying the guide catheter through a sheath. Further, it would be desirable to facilitate the exchange of guide catheters while providing sheathless access. Still further, it would be desirable to allow the use of any guide catheter of choice, such as of any size, shape and/or manufacturer. As will be described in the following materials, this disclosure satisfies these and other needs.

SUMMARY

The present disclosure is directed to a dilator for gaining access to a vessel of a patient, comprising an elongated body with proximal and distal ends, a distal portion with a maximal outer diameter that extends from the distal end to a guidewire exit port, a proximal portion with a reduced profile that extends from the guidewire exit port to the proximal end and a lumen that extends between the distal end and the guidewire exit port. The reduced profile proximal portion may have a smaller cross sectional area than the maximal diameter distal portion. For example, the reduced profile proximal portion may have a cross sectional area at least 40% smaller than the maximal diameter distal portion. The cross sectional area may further be at least 50% smaller than the maximal diameter distal portion.

In one aspect, the reduced profile proximal portion may have a semi-cylindrical configuration and the maximal diameter distal portion may have a cylindrical configuration.

The disclosure also includes a kit for gaining access to a vessel of a patient. The kit may include a first dilator having an elongated body with proximal and distal ends, a distal portion with a maximal outer diameter that extends from the distal end to a guidewire exit port, a proximal portion with a reduced profile that extends from the guidewire exit port to the proximal end and a lumen that extends between the distal end and the guidewire exit port and a second dilator having an elongated body with proximal and distal ends, a distal portion with a maximal outer diameter that extends from the distal end to a guidewire exit port, a proximal portion with a reduced profile that extends from the guidewire exit port to the proximal end and a lumen that extends between the distal end and the guidewire exit port.

In one aspect, the lumen of the first dilator may have a smaller inner diameter than the lumen of the second dilator. The maximal outer diameter distal portion of the first dilator may have an outer diameter the same as the maximal outer diameter distal portion of the second dilator. Alternatively, the maximal outer diameter distal portion of the first dilator may have an outer diameter smaller than the maximal outer diameter distal portion of the second dilator.

The disclosure also includes a method for gaining access to a vessel of a patient. The method may involve providing a first dilator having an elongated body with proximal and distal ends, a distal portion with a maximal outer diameter that extends from the distal end to a guidewire exit port, a proximal portion with a reduced profile that extends from the guidewire exit port to the proximal end and a lumen that extends between the distal end and the guidewire exit port, positioning a first guidewire within the vessel of the patient, advancing the first dilator over the first guidewire into the vessel without being inserted through a sheath, advancing a first guide catheter over the first dilator and removing the first dilator. The first dilator may be preloaded into the first guide catheter before advancing the first dilator.

In one aspect, the method may also involve introducing a second guidewire through the first guide catheter and positioning a distal end of the second guidewire at a desired region of within the patient, wherein the second guidewire has a larger diameter than the first guidewire. At least a portion of a procedure may be performed with the first guide catheter.

In one aspect, the method may also involve withdrawing the first guide catheter, providing a second dilator having an elongated body with proximal and distal ends, a distal portion with a maximal outer diameter that extends from the distal end to a guidewire exit port, a proximal portion with a reduced profile that extends from the guidewire exit port to the proximal end and a lumen that extends between the distal end and the guidewire exit port, advancing the second dilator over the second guidewire into the vessel without being inserted through a sheath, advancing a second guide catheter over the second dilator and removing the second dilator. The second dilator may be preloaded into the second guide catheter before advancing the first dilator.

In one aspect, the method may also involve performing at least a portion of the procedure with the second guide catheter.

In one aspect, the vessel may be a radial artery.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which.

DETAILED DESCRIPTION

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner.

Unless defined otherwise, all technical and scientific terms used herein have the same meaning as commonly understood by one having ordinary skill in the art to which the disclosure pertains.

Finally, as used in this specification and the appended claims, the singular forms "a, "an" and "the" include plural referents unless the content clearly dictates otherwise.

As noted above, transradial catheterization offers significant benefits over femoral approaches due to the potential for reduced complications. By employing the techniques of this disclosure, the use of a sheath may be avoided when introducing a guide catheter into a vessel of the patient, such as the radial artery. Since a sheath is not required, a correspondingly larger diameter guide catheter may be employed. For a majority of coronary interventions, a 6 French guide catheter is required. While the median radial artery diameter ranges from 1.9 mm to 2.5 mm in different ethnic populations, conventional use of a 2.5 mm access (6 French sheath) is more likely to lead to above-mentioned problems.

While sheaths were originally designed for femoral artery access, differences in anatomy and physiology of the arteries such as radial artery and pedal artery may preclude the need to employ a sheath for access. Thus, sheathless access in to an artery may be used to carry out every catheterization task and may allow use of a guide catheter having an outer diameter that is significantly smaller than that which would be required when using a respective sheath size. For example, entry with a guide catheter instead of a sheath may be accomplished with a smaller overall diameter for a respective French size, such as 0.5 mm or smaller. In turn, this reduces the potential for stretching or expanding the artery and likewise may reduce irritation, inflammation, pain and/or the chance of iatrogenic artery occlusion. As such, these techniques may be employed to reduce the size of entry in any catheterization procedure, including those for transradial, transbrachial, transfemoral and transpedal access as well as others.

The techniques of this disclosure permit transradial access, for example, while avoiding the need of using a sheath completely and is therefore a true sheathless access that may be used for diagnostic as well as all kinds of coronary intervention procedures and peripheral procedures. Notably, these techniques work in every patient with a smaller size puncture (hole) for the respective catheter size required. Most diagnostic and many intervention procedures may be performed by 1.67 mm (5 French) guide catheter with sheathless access, and, if required, the same access may be expanded to a larger size, such as a 2.00 mm (6 French) or a 2.32 mm (7 French) guide catheter. Even for such increased sizes, the use of a correspondingly larger sheath is avoided to reduce radial access size in every procedure and thereby reduce or even eliminate the limitations of radial access, such as spasm, pain, injury, radial occlusion, and the inability to perform complex interventions. Embodiments of the present disclosure may solve all the above-mentioned problems related to transradial catheterization.

Figure 1:
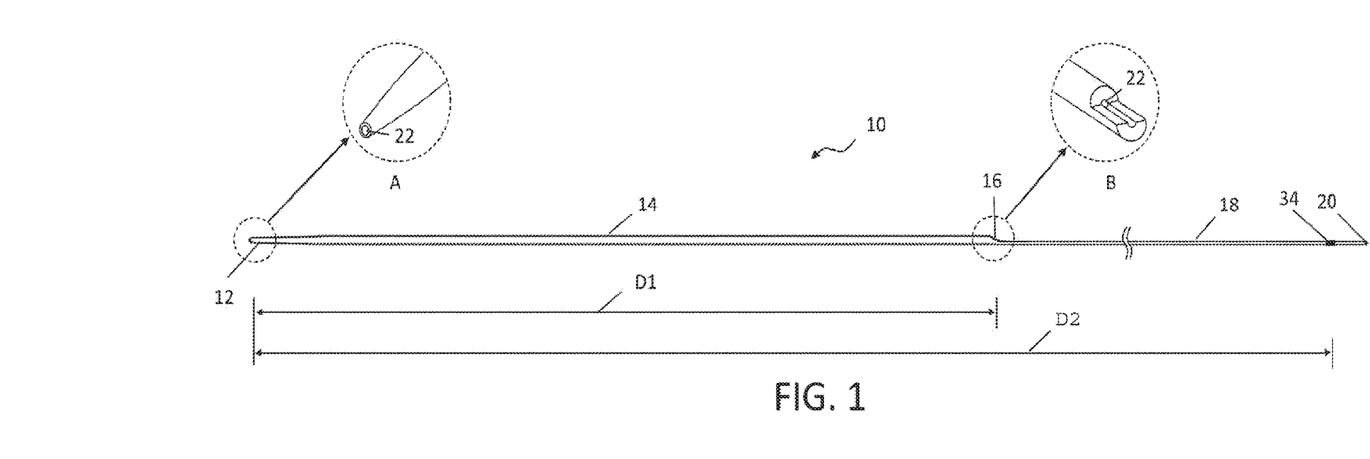
FIG. 1 is an elevational view of a first dilator to be advanced over a first guidewire for sheathless access of a vessel, according to one embodiment.

To help illustrate aspects of this disclosure, an exemplary embodiment of a radial access dilator is shown schematically in FIG. 1 in an elevational view. As shown, first radial access dilator 10 is an elongated member having a tapered distal end 12, with an outer diameter that increases to a maximal outer diameter in distal portion 14. The maximal outer diameter may be selected to closely conform to the inner diameter of the guide catheter to be used. The diameter may be constant throughout distal portion 14 until first radial access dilator 10 transitions to a reduced profile at guidewire exit port 16. Proximal portion 18 of radial access dilator 10 extends from guidewire exit port 16 to proximal end 20. Guidewire lumen 22 extends from distal end 12, as shown in the perspective view of inset detail A, to guidewire exit port 16, as shown in the perspective view of inset detail B. Guidewire lumen 22 may exhibit a constant inner diameter along its length and may be sized to closely conform to the outer diameter of a first guidewire to be used with first radial access dilator 10. Inset detail B also shows the transition of first radial access dilator 10 from its maximal outer diameter to the reduced profile. In this embodiment, distal portion 14 has a cylindrical configuration corresponding to the maximal outer diameter while proximal portion 18 has a semi-cylindrical configuration. However, other shapes and configurations may be employed as desired. As will be appreciated, the reduced profile of proximal portion 18 has a smaller cross sectional area of material as compared to the maximal outer diameter of distal portion 14. In one aspect, the smaller cross sectional area may represent a reduction in the range of approximately 40-60%, such as approximately 50%. Since the reduced profile proximal portion 18 represents a significant proportion of the overall length of radial access dilator 10, it may create less friction with a guide catheter, facilitating advancement of the guide catheter over radial access dilator 10.

Figure 2:
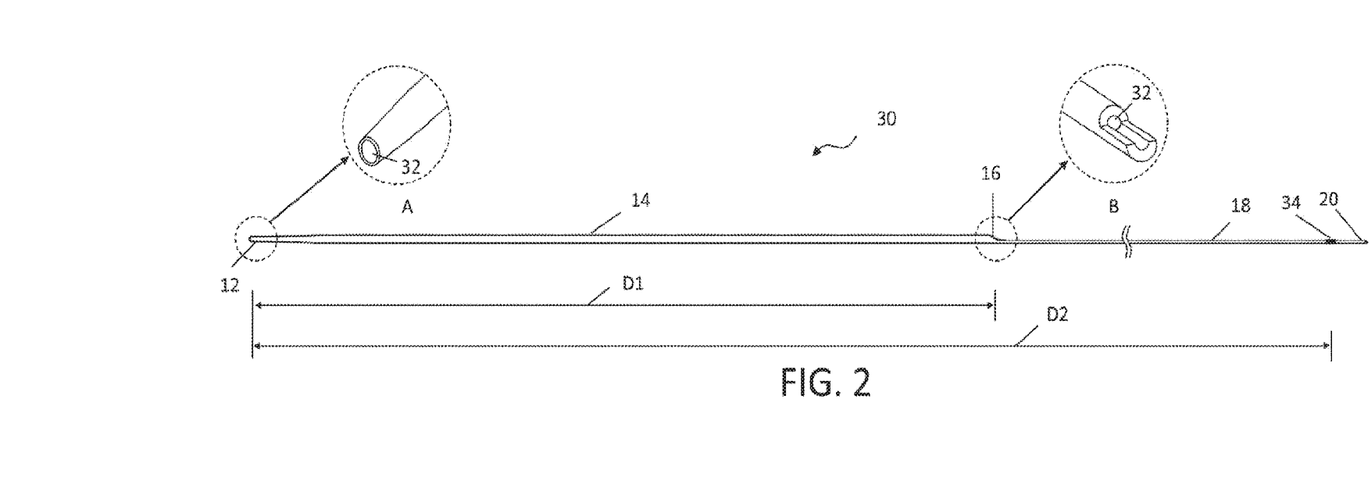
FIG. 2 is an elevational view of a second dilator to be advanced over a second guidewire for sheathless access of a vessel, according to one embodiment.

As will be described in further detail below, exchange of guide catheters may be accomplished through the use of a second radial access dilator 30, which is depicted in FIG. 2. The overall design of radial access dilator 30 is similar to radial access dilator 10, so many of the elements are described with the same reference numbers. For example, second radial access dilator 30 is also an elongated member having a tapered distal end 12, with a maximal outer diameter in distal portion 14. Notably, the maximal outer diameter may be the same for both radial access dilator 10 and radial access dilator 30, so that guide catheter having the same inner diameter may readily be exchanged. Second radial access dilator 30 also transitions to a reduced profile at guidewire exit port 16, with proximal portion 18 extending to proximal end 20. Significantly, guidewire lumen 32, which extends from distal end 12, as shown in the perspective view of inset detail A, to guidewire exit port 16, as shown in the perspective view of inset detail B, may exhibit a constant inner diameter along its length and may be sized to closely conform to the outer diameter of a second guidewire, such that the second guidewire has a greater diameter than the first guidewire. Also similar to radial access dilator 10, distal portion 14 of radial access dilator 30 has a cylindrical configuration corresponding to the maximal outer diameter while proximal portion 18 has a semi-cylindrical configuration, but other configurations may be employed, so that the reduced profile of proximal portion 18 has a smaller cross sectional area of material as compared to the maximal outer diameter of distal portion 14. With radial access dilator 30, the smaller cross sectional area may also represent a reduction in the range of approximately 40-60%, such as approximately 50%.

Both radial access dilator 10 and radial access dilator 30 may be formed from any suitable polymeric material having the desired characteristics. In some embodiments, nylon (polyamide), urethane, polypropylene, as well as polyamide co-polymers such as, for example, polyether block amides (PEBAX®), or others may be employed. Further, the relative dimensions of radial access dilator 10 and radial access dilator 30 may be selected as desired. In one embodiment, both radial access dilator 10 and radial access dilator 30 may have an overall length of approximately 130 cm, so as to extend approximately 10-20 cm from the proximal end of the guide catheter when preloaded for introduction into the vessel. With this configuration, the proximal ends of both the guide catheter and the dilator may be manipulated during introduction and advancement. Accordingly, a suitable range for the length of either or both radial access dilator 10 and radial access dilator 30 is approximately 130 to 140 cm in some embodiments and may be other lengths as desired depending on the procedure and/or the artery being accessed. The maximal outer diameter of radial access dilator 10 and radial access dilator 30 may correspond to the inner diameter of the guide catheter(s) being used in the procedure. For example, for a 6 French guide catheter, the maximal outer diameter may be approximately 1.80 mm, with corresponding adjustment for other sizes. The inner diameter of lumens 22 and 32 may also be selected based on the diameters of the first and second guidewires being used during the exchange procedure. In one embodiment, lumen 22 of radial access dilator 10 may have a diameter corresponding to a 0.021" (0.58 mm) guidewire and lumen 32 of radial access dilator 30 may have a diameter corresponding to a 0.035" (0.88 mm) guidewire, although different guidewires having other diameters may be employed as desired.

The distance to guidewire exit port 16 may be tailored to the desired application and, in some embodiments, may be the same for both radial access dilator 10 and radial access dilator 30. For example, the distance from distal end 12 to guidewire exit port for radial access dilator 10, as indicated by D1 in FIG. 1, may be approximately 30 cm and the distance from distal end 12 to guidewire exit port for radial access dilator 30, as indicated by D1 in FIG. 2, may also be approximately 30 cm. Depending on the procedure and/or the vessel being accessed, these distances may be adjusted as desired. An exemplary range for either or both radial access dilator 10 and radial access dilator 30 for D1 is 15 cm to 35 cm. It will be appreciated that either or both radial access dilator 10 and radial access dilator 30 may be advanced only a relatively short distance into the patient's vasculature relative to the location where the procedure is to be performed, which in some embodiments may be in the range of 20 to 40 cm. For example, guidewire exit port 16 may remain outside the patient's body. As such, guidewire exit port 16 may be located relatively closer to distal end 12 than proximal end 20. A relatively smooth, atraumatic transition between the maximal outer diameter portion 14 and the outer diameter of the guide catheter is formed due to the close conformance of the outer diameter of the dilator and the inner diameter of the guide catheter, facilitating the advancement of the guide catheter over the dilator. Once the guide catheter has been suitably advanced, such as so that its distal end is adjacent the junction between tapered distal end 12 and maximal outer diameter portion 14, the dilator may be removed. In one aspect, this may correspond to proximity between marker 34 or any other suitable indicator and any suitable reference point relative to the proximal end of the guide catheter. Tapered distal end 12 may be about four cm in length to provide smooth transition or dilation of the skin, subcutaneous tissue and artery wall. If desired, some or all of both radial access dilator 10 and radial access dilator 30 may have a hydrophilic coating to facilitate introduction and advancement through the patient's vasculature as well as to reduce friction when a guide catheter is advanced over the dilator. In one aspect, tapered distal end 12 and proximal portion 14 of either or both radial access dilator 10 and radial access dilator 30 may have a hydrophilic coating.

Further, either of both radial access dilator 10 and radial access dilator 30 may feature one or markers 34 at a suitable distance from distal end 12 as indicated by D2 in FIG. 1 for radial access dilator 10 and as indicated by D2 in FIG. 2 for radial access dilator 30. Markers 34 may be positioned at distances D2 of either or both of 93 cm and 103 cm, or at other suitable locations as desired.

One suitable technique for employing one or both radial access dilator 10 and radial access dilator 30 for transradial catheterization, including exchange of guide catheters if desired is schematically represented in FIGS. 3-13. In the following materials, the technique is described in the context of specific guide catheter and guidewire sizes while providing transradial access, but one of ordinary skill in the art will recognize that it may be extended to cover use of other sizes of guide catheters and guidewires and may be used for access to other vessel in a patient.

Figure 3:
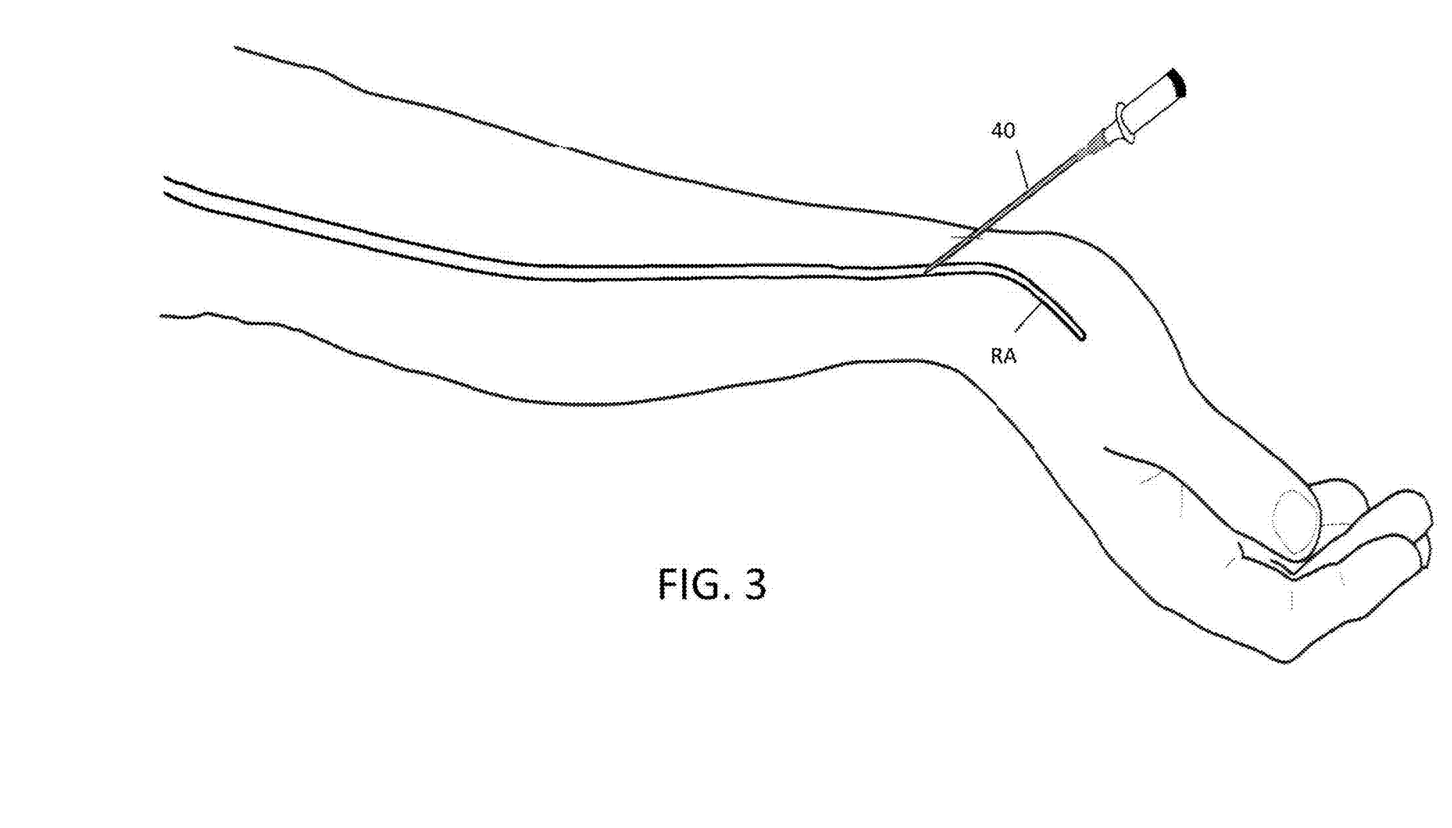
FIG. 3 is a schematic view showing achieving radial access with a needle, according to one embodiment.
Figure 4:
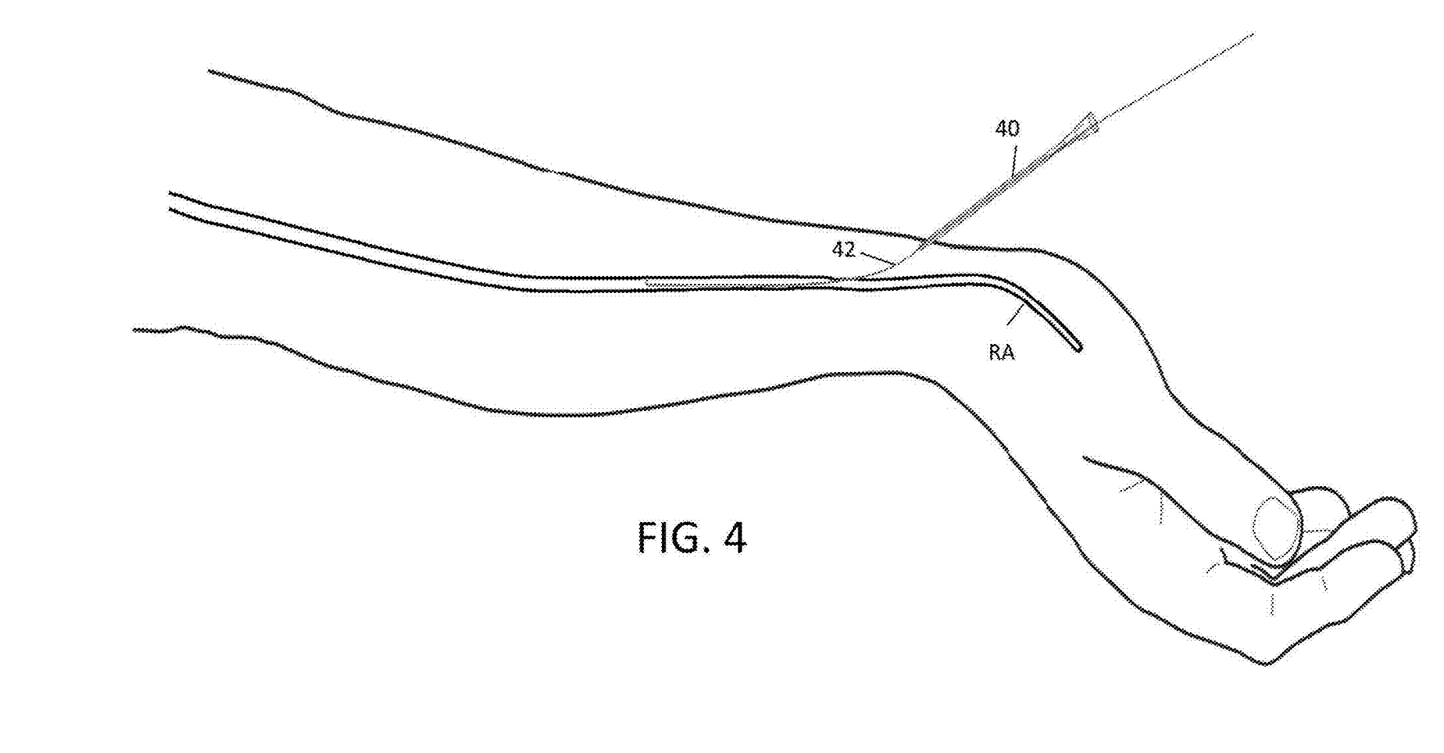
FIG. 4 is a schematic view showing insertion of a first guidewire into a radial artery, according to one embodiment.
Figure 5:
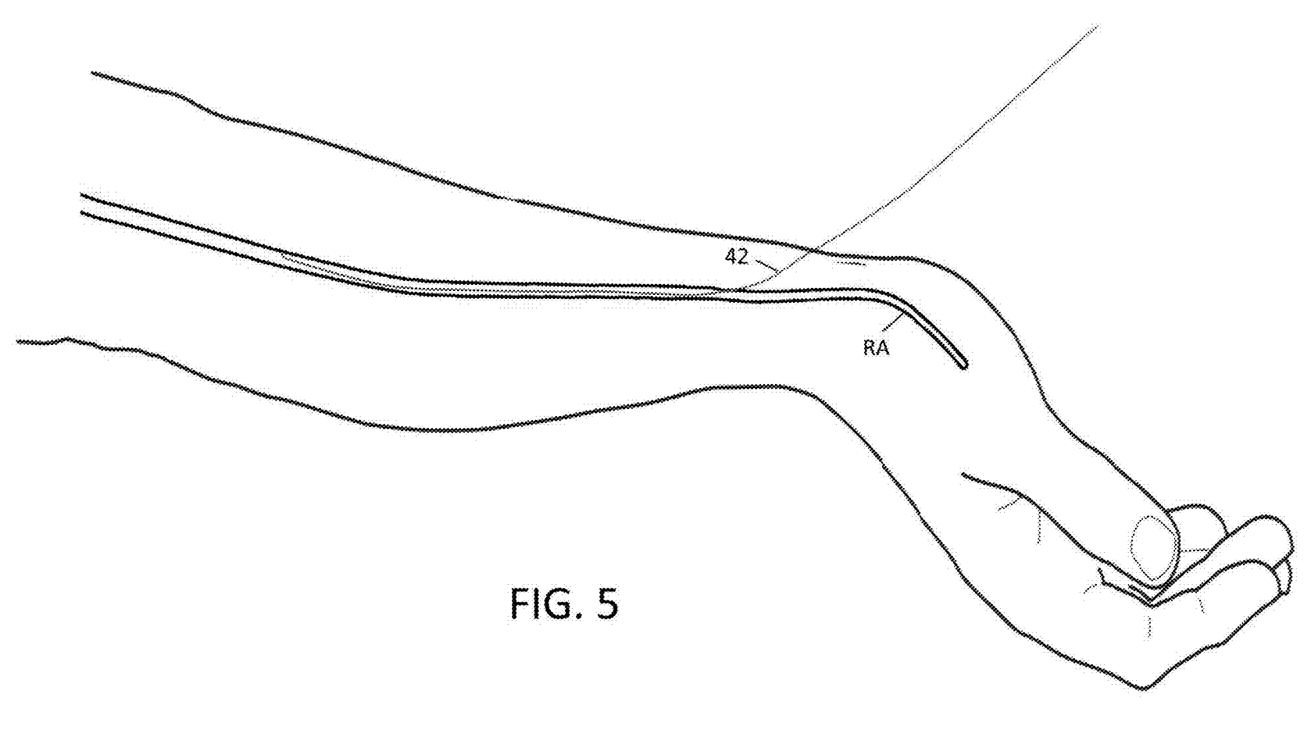
FIG. 5 is a schematic view showing removal of the needle, according to one embodiment.

Beginning with FIG. 3, transradial access is achieved by palpation or ultrasound guidance per the operator's choice. The radial artery (RA) is punctured using a 21-gauge needle 40. An anterior or posterior puncture can be performed by either using a bare needle or intra-cath venous access needle, respectively. In either case, once the pulsatile blood flow is seen, a 0.021 inch guidewire 42 is inserted in the radial artery as indicated by FIG. 4. Guidewire 42 may be approximately 40 cm in some embodiments, although different lengths and diameters may be used as desired. Needle 40 is removed while securing guidewire 42 in the radial artery lumen and hemostasis is achieved as shown in FIG. 5. As noted radial access dilator 10 has an outer diameter similar to that of the inner diameter of the guide catheter intended to use (e.g., for a 6 French guide, the maximal outer diameter of radial access dilator 10 is 1.80 mm), and is about 130 cm long.

Figure 6:
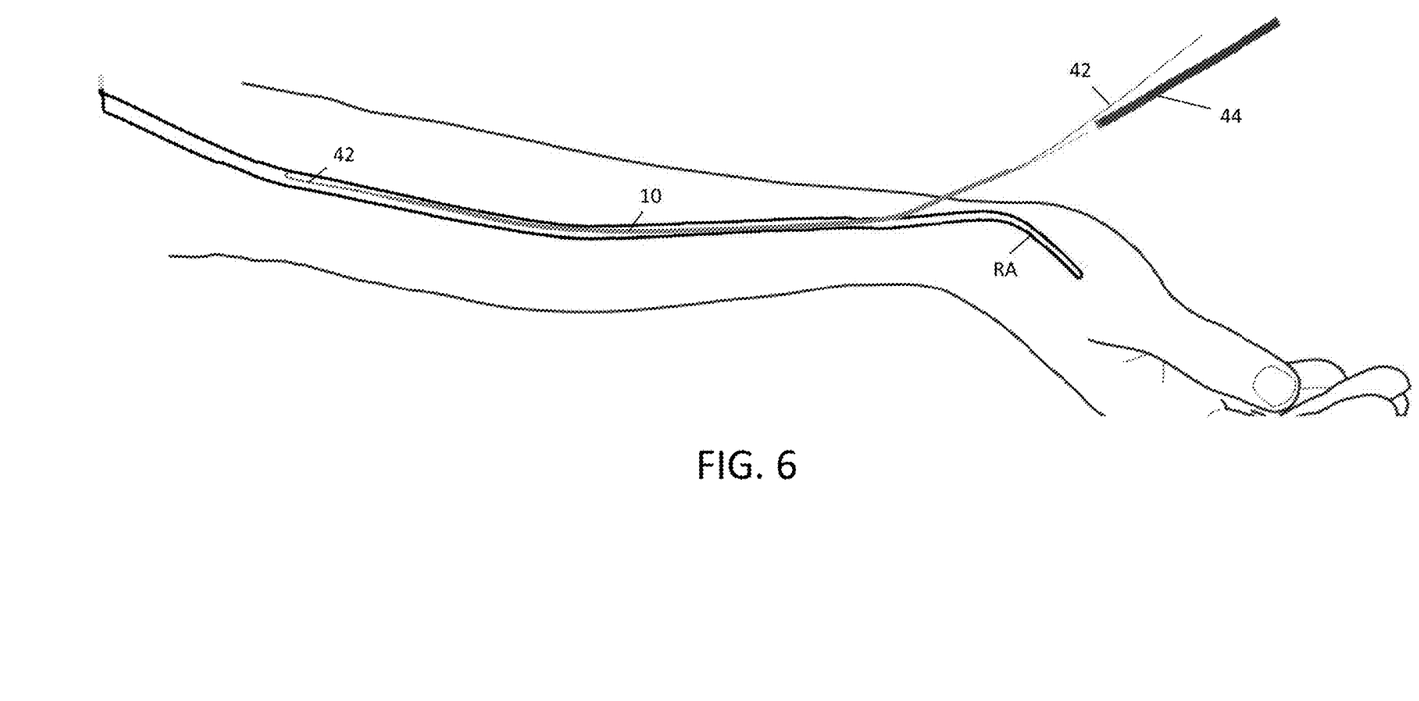
FIG. 6 is a schematic view illustrating preloading a first guide catheter over the first dilator and advancing the assembly into the radial artery, according to one embodiment.
Figure 7:
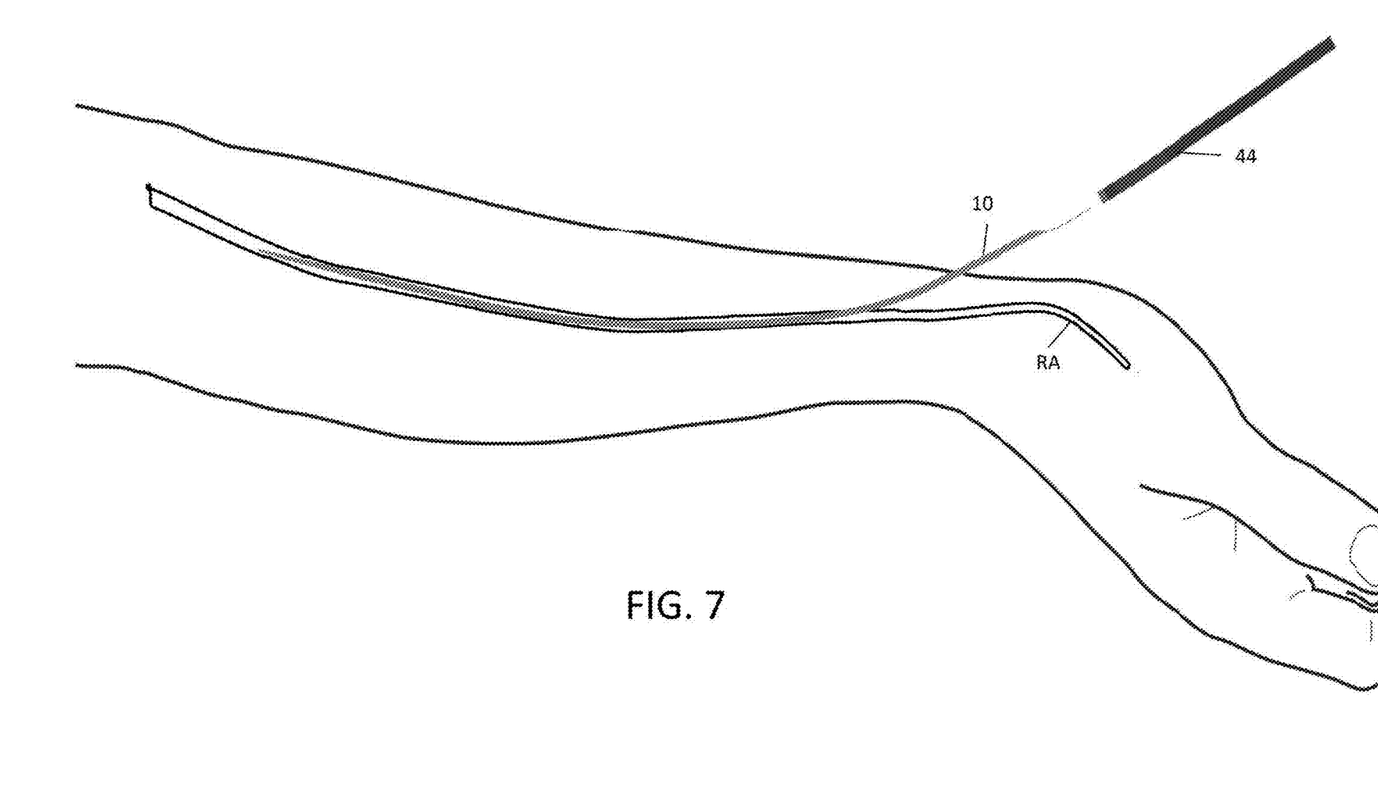
FIG. 7 is a schematic view showing removal of the first guidewire, according to one embodiment.
Figure 8:
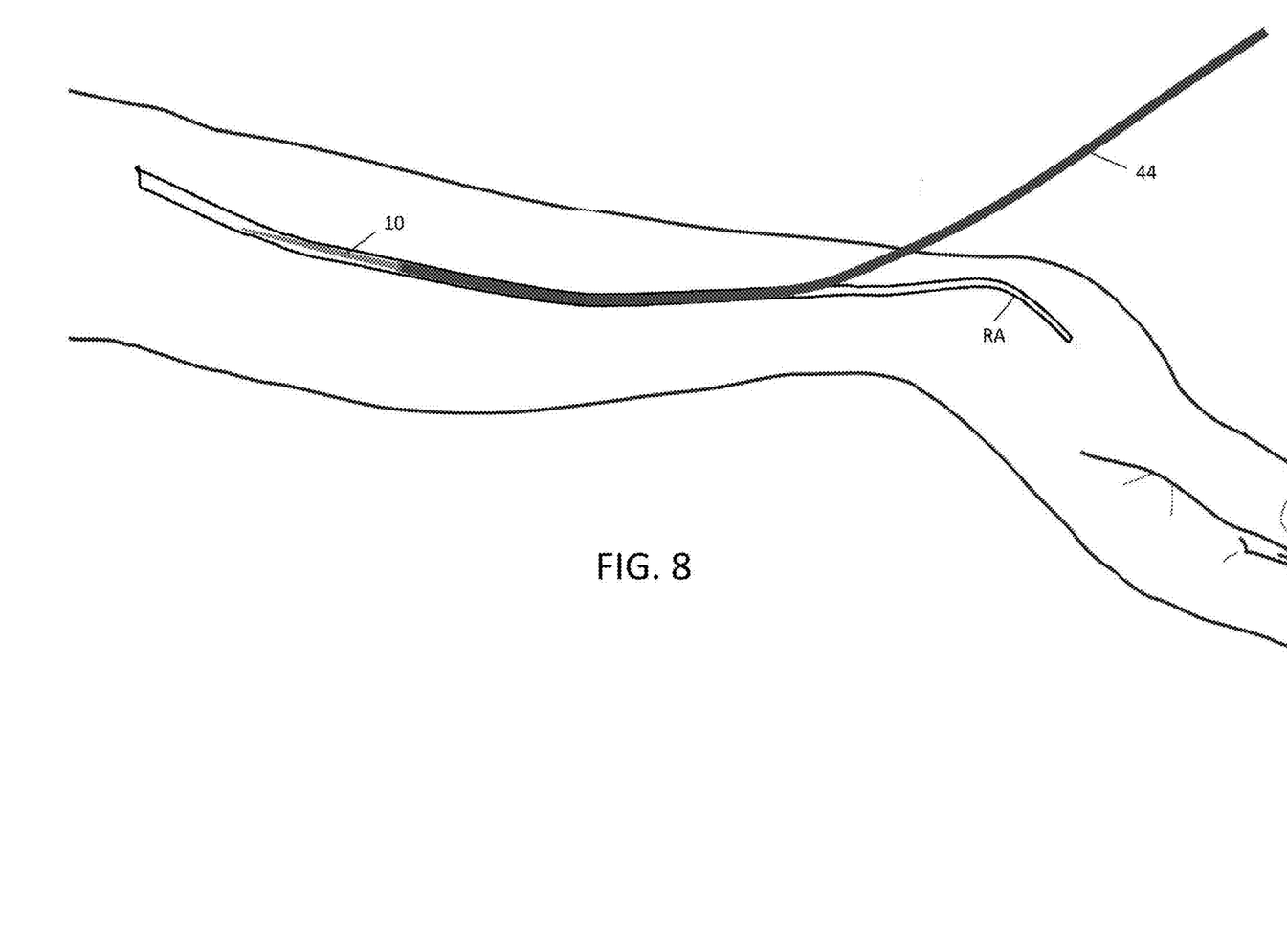
FIG. 8 is a schematic view showing a first guide catheter advanced over the first dilator up to the distal marker, according to one embodiment.
Figure 9:
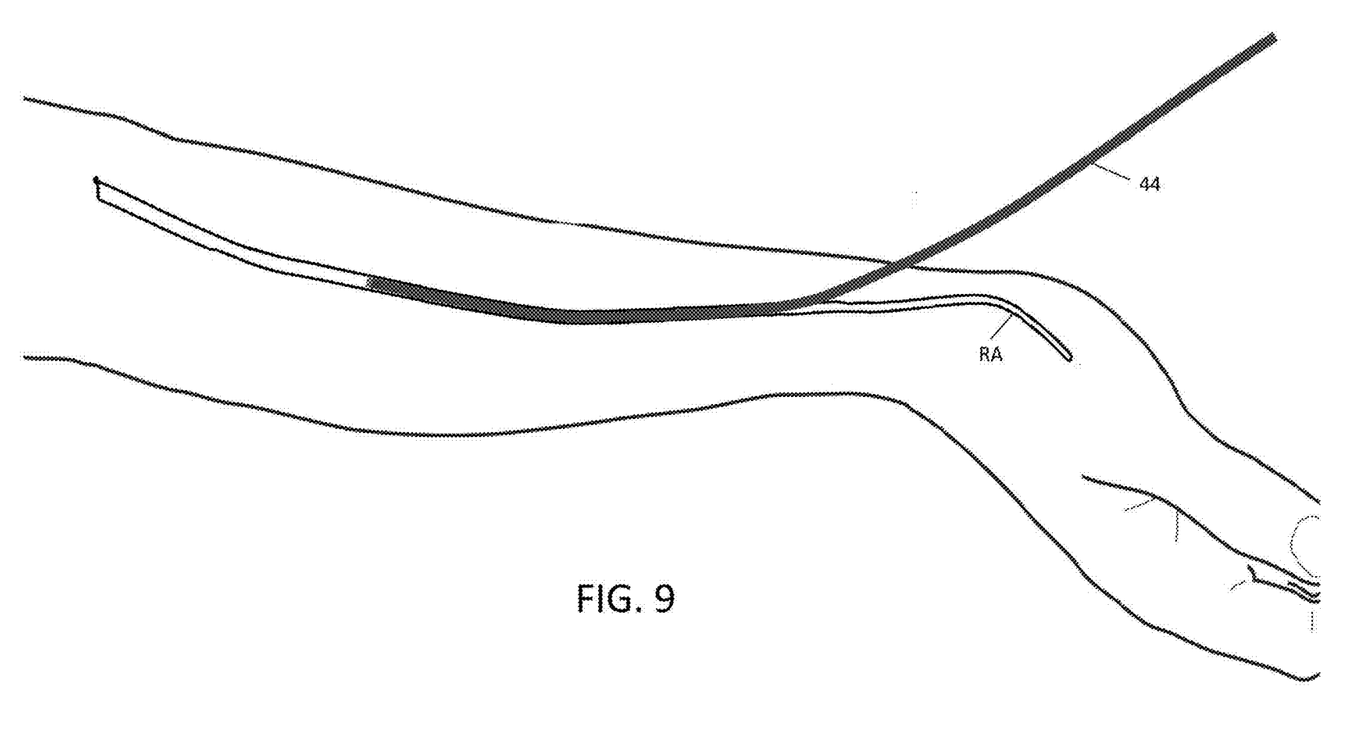
FIG. 9 is a schematic view illustrating the removal of the first dilator, according to one embodiment.
Figure 10:
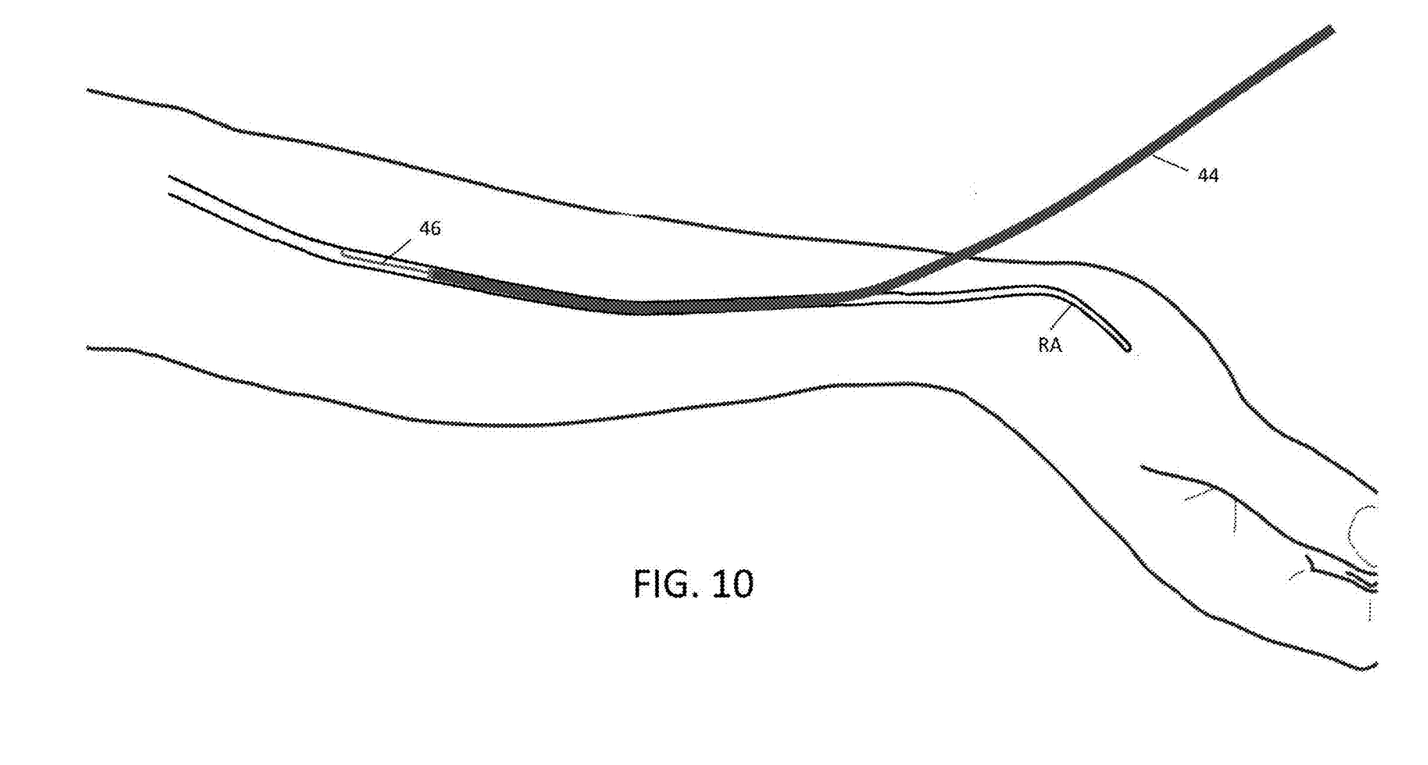
FIG. 10 is a schematic view showing a second guidewire inserted and the first guide catheter advanced over the second guidewire, according to one embodiment.

The guide catheter 44 of operator's choice will be preloaded on radial access dilator 10, which may then be advanced over guidewire 42 in to the radial artery as shown in FIG. 6. After advancing the first 30 cm of radial access dilator 10, guidewire 42 will exit from guidewire exit port 16. Guidewire 42 may then be removed as shown in FIG. 7 and guide catheter 44 may then be advanced into the radial artery over radial access dilator 10 as shown in FIG. 8. A suitable distal marker, such as marker 34, may help indicate the relative position of radial access dilator 10 within the vasculature. A tapered, hydrophilic guide catheter 44 may be used to facilitate entry into the radial artery. As will be appreciated, due to the similarity in size between the inner diameter of guide catheter 44 and the maximal outer diameter of radial access dilator 10, a smooth transition is achieved. After advancing the guide catheter for approximately 25-30 cm, radial access dilator 10 may be removed as shown in FIG. 9. Next, a 0.035 inch guidewire 46 may be inserted through guide catheter 44, similar to current standard transradial catheterization, and advanced to an area corresponding to the procedure being performed. Guidewire 46 may have a J configuration as shown and may have a length of approximately 260 cm, although different lengths and diameters may be used as desired. Guide catheter 44 is advanced over guidewire 46 in to the ascending aorta, descending aorta or other location, again depending on the procedure being performed and used to perform intended procedure.

Figure 11:
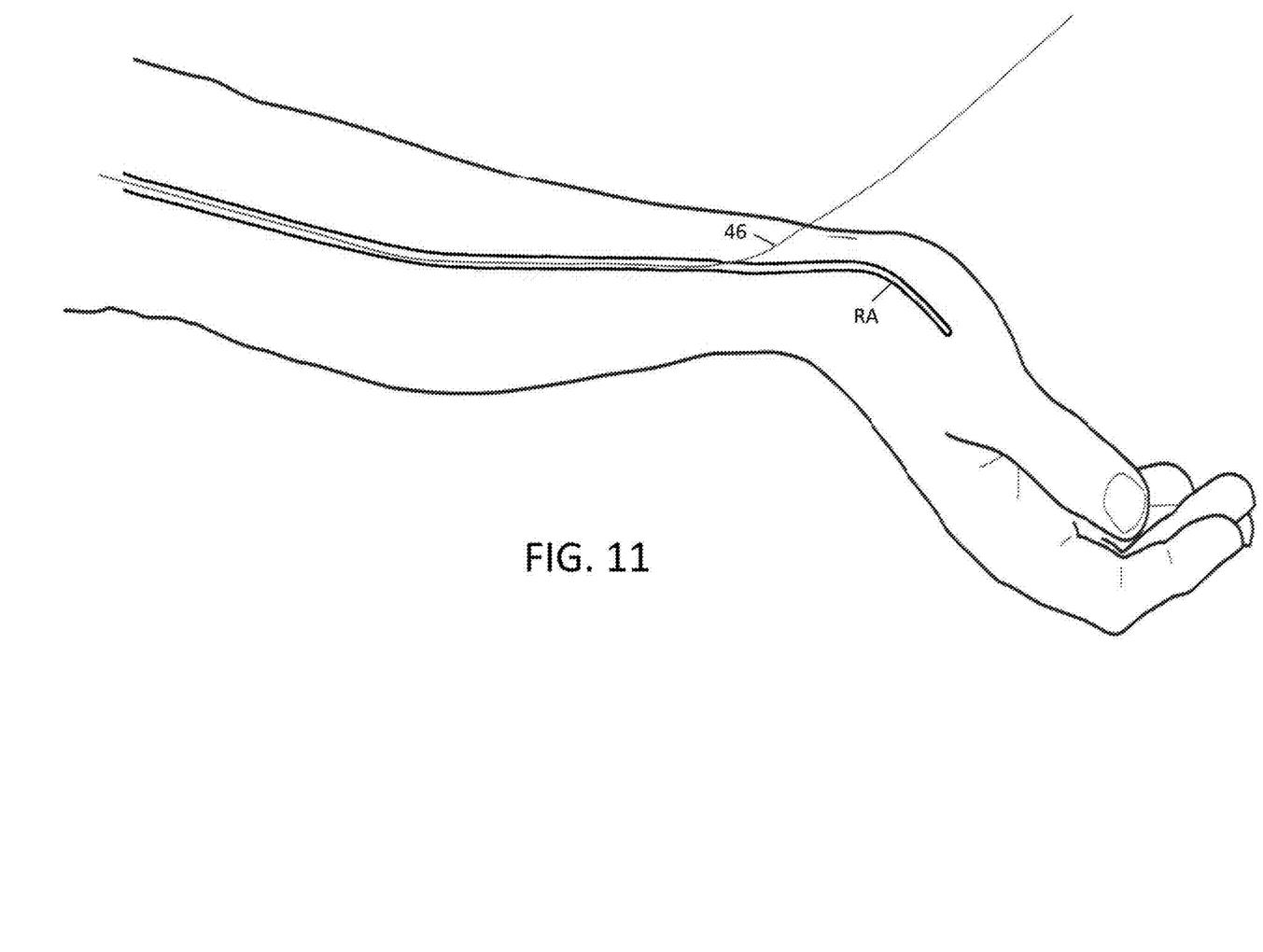
FIG. 11 is a schematic view illustrating the first guide catheter being removed for exchange, according to one embodiment.
Figure 12:
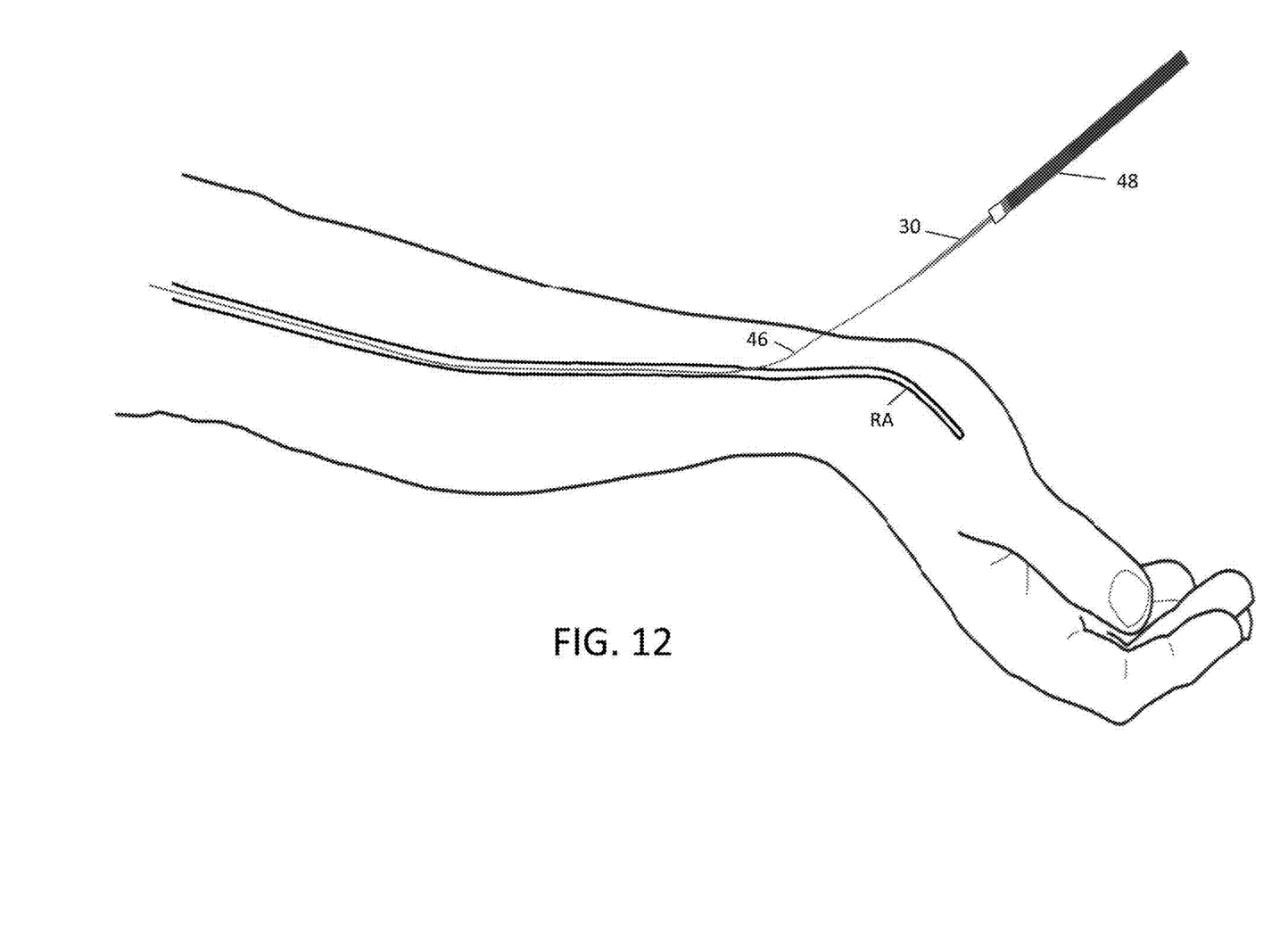
FIG. 12 is a schematic view illustrating a second guide catheter being loaded over the second dilator, according to one embodiment.
Figure 13:
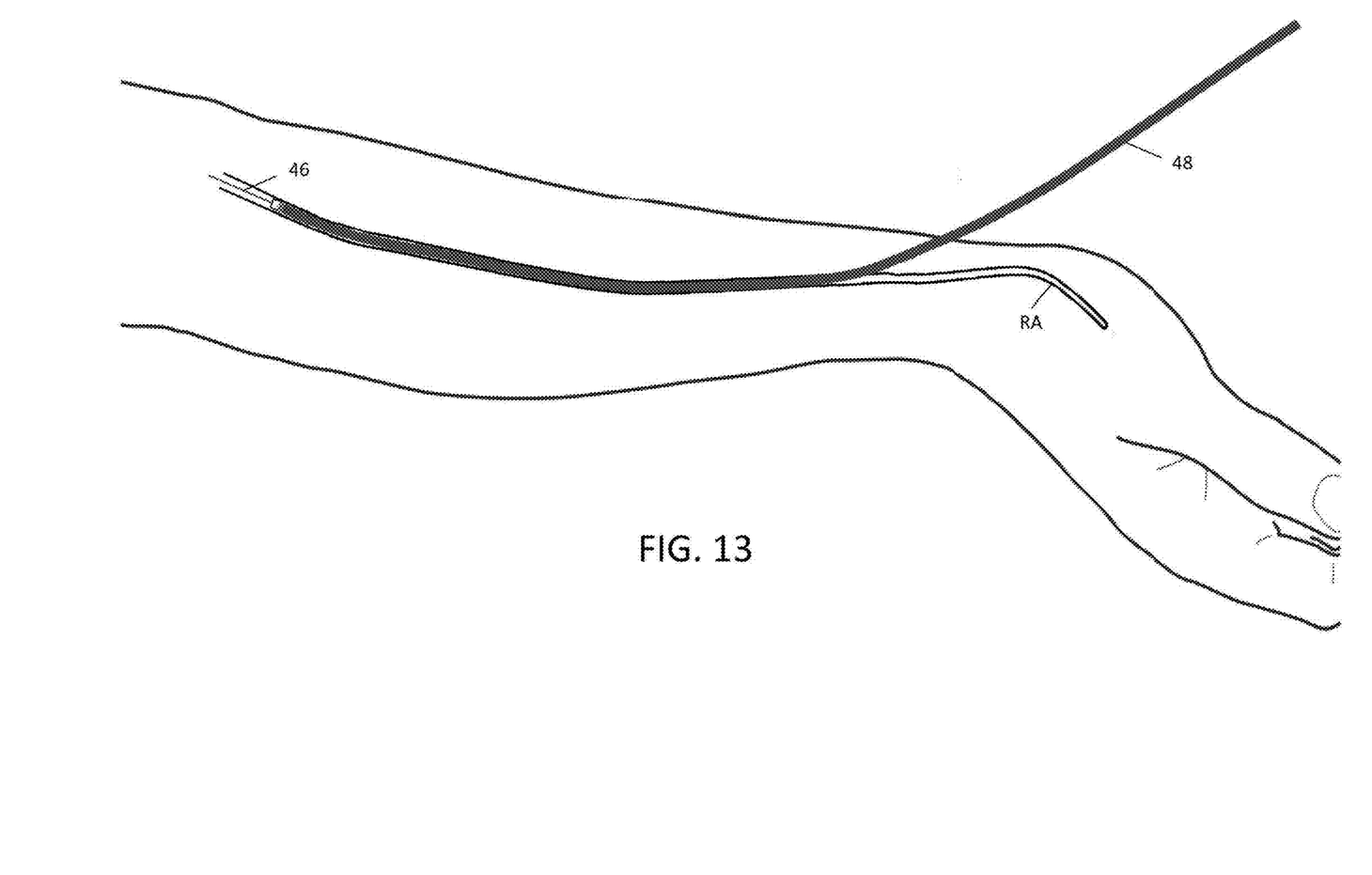
FIG. 13 is a schematic view illustration the second guide catheter and second dilator being inserted into a radial artery, according to one embodiment.

If the operator needs to use a different shape or larger size guide catheter, guidewire 46 may be maintained in its advanced location, or if it has been removed, it may be advanced again through guide catheter 44. Guide catheter 44 may then be removed as shown in FIG. 11 and hemostasis is achieved by applying gentle pressure on the wrist. Radial access dilator 30 is preloaded into new guide catheter 48 and threaded over guidewire 46 in place. As noted, radial access dilator 30 has lumen 32 that corresponds to guidewire 46 and may have the same maximal outer diameter as radial access dilator 10 if guide catheter 48 is of the same size, or may have a correspondingly greater maximal outer diameter to closely conform to the inner diameter of guide catheter 48 if larger. Radial access dilator 30 and guide catheter 48 may then be advanced into the radial artery and to the treatment area over guide wire 46 as shown in FIG. 12. Radial access dilator 30 may then be removed as shown in FIG. 13, to allow guide catheter 48 to be used to continue the procedure. After completing the procedure the guide catheter is removed and a radial hemostatic band can be applied similar to current practice of patent hemostasis.

As will be appreciated from the above description, access to the radial artery using either or both radial access dilator 10 and radial access dilator 30 may be accomplished with at least a 0.5 mm smaller hole and a smaller intrusion into the radial artery as compared to conventional entry with a sheath. For example, a 6 French sheath will lead to 2.61 mm puncture in radial artery while using radial access dilator 10, the radial artery puncture and the maximal diameter of a device to be inserted in the artery may be reduced to approximately 2.00 mm. In this manner, most or all patients will be able to tolerate the use of a 6 French guide catheter, with considerably less trauma. Further, a 7 French guide catheter (outer diameter 2.3 mm) may be used with a greater proportion of patients, so that more complex coronary procedures and peripheral procedures may be performed. In other procedures, a 5 French guide catheter may be employed. Regardless of the size of the guide catheter, the requirement of a smaller hole and avoidance/reduction of expansion and/or irritation of the radial artery as compared to access with a sheath will reduce or eliminate, spasm, pain, inflammation and occlusion, and allow a successful trans-radial catheterization. As noted, the techniques of the this disclosure allow the operator to use any guide catheter of any shape or size, by any manufacturer, and allows the operator to exchange guide catheters as many times as required without additional cost (equipment). Since the techniques provide a true sheathless access and do not require any radial sheath, substantial cost savings may be realized in addition to the reduction in invasiveness of the procedure.

The preceding description has been presented with reference to presently disclosed embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A kit for gaining access to a vessel of a patient, comprising:
   a first dilator having an elongated body with proximal and distal ends, a distal portion with a maximal outer diameter having a cylindrical configuration that extends from the distal end to a guidewire exit port, a proximal portion with a reduced profile having a semi-cylindrical configuration that extends from the guidewire exit port to the proximal end and a lumen defined by an inner wall that extends between the distal end and the guidewire exit port, wherein a portion of the inner wall continues to extend through the proximal portion; and
   a second dilator having an elongated body with proximal and distal ends, a distal portion with a maximal outer diameter having a cylindrical configuration that extends from the distal end to a guidewire exit port, a proximal portion with a reduced profile having a semi-cylindrical configuration that extends from the guidewire exit port to the proximal end and a lumen defined by an inner wall that extends between the distal end and the guidewire exit port, wherein a portion of the inner wall continues to extend through the proximal portion;
   wherein the first dilator is configured to be inserted into a radial artery, and the second dilator is configured to be inserted into the radial artery upon removal of the first dilator;
   wherein the lumen of the first dilator has a smaller inner diameter than the lumen of the second dilator; and
   wherein the maximal outer diameter distal portion of the first dilator has an outer diameter the same as the maximal outer diameter distal portion of the second dilator.

2. The kit of claim 1, wherein the maximal outer diameter of the first dilator is about 1.80 mm.

3. The kit of claim 1, further comprising a marker positioned on the proximal portion of the first dilator.

4. The kit of claim 1, wherein the lumen of the first dilator has a diameter of about 0.58 mm and the lumen of the second dilator has a diameter of about 0.88 mm.

5. The kit of claim 1, wherein the reduced profile proximal portion of the first dilator has a cross sectional area at least 40% smaller than a cross sectional area of the maximal outer diameter distal portion of the first dilator.

6. The kit of claim 5, wherein the reduced profile proximal portion of the first dilator has a cross sectional area at least 50% smaller than a cross sectional area of the maximal outer diameter distal portion of the first dilator.

7. The kit of claim 1, wherein the semi-cylindrical configuration of the proximal portion of the first dilator is configured to receive a guidewire therein and the cylindrical configuration of the distal portion of the first dilator is configured to receive the guidewire in the lumen therein.

8. The kit of claim 1, wherein the maximal outer diameter of the second dilator is about 1.80 mm.

9. The kit of claim 1, wherein the distal end of the first dilator is tapered.

10. The kit of claim 9, wherein the tapered distal end of the first dilator has a hydrophilic coating.

11. The kit of claim 1, wherein the distal end of the second dilator is tapered.

12. The kit of claim 11, wherein the tapered distal end of the second dilator has a hydrophilic coating.

13. The kit of claim 1, wherein the first and second dilators are formed from a polymeric material.

14. A method for gaining access to a radial artery of a patient, comprising:
    providing a first dilator having an elongated body with proximal and distal ends, a distal portion with a maximal outer diameter having a cylindrical configuration that extends from the distal end to a guidewire exit port, a proximal portion with a reduced profile having a semi-cylindrical configuration that extends from the guidewire exit port to the proximal end and a lumen that extends between the distal end and the guidewire exit port;
    positioning a first guidewire within the radial artery of the patient;
    advancing the first dilator over the first guidewire into the radial artery without being inserted through a sheath;
    advancing a first guide catheter over the first dilator;
    removing the first dilator;
    providing a second dilator having an elongated body with proximal and distal ends, a distal portion with a maximal outer diameter having a cylindrical configuration that extends from the distal end to a guidewire exit port, a proximal portion with a reduced profile having a semi-cylindrical configuration that extends from the guidewire exit port to the proximal end and a lumen that extends between the distal end and the guidewire exit port; and introducing the second dilator through the first guide catheter and positioning a distal end of the second dilator at a desired region of the radial artery, wherein the lumen of first dilator has a smaller inner diameter than a lumen of the second dilator;

wherein the maximal outer diameter distal portion of the first dilator has an outer diameter the same as the maximal outer diameter distal portion of the second dilator.

15. The method of claim 14, further comprising preloading the first dilator into the first guide catheter before advancing the first dilator.

16. The method of claim 14, further comprising introducing a second guidewire through the first guide catheter and positioning a distal end of the second guidewire at a desired region of the radial artery, wherein the second guidewire has a larger diameter than the first guidewire.

17. The method of claim 16, further comprising performing at least a portion of a procedure with the first guide catheter.

18. The method of claim 17, further comprising:
withdrawing the first guide catheter;
advancing the second dilator over the second guidewire into the vessel without being inserted through a sheath;
advancing a second guide catheter over the second dilator; and
removing the second dilator.

19. The method of claim 18, further comprising preloading the second dilator into the second guide catheter before advancing the first dilator.

20. The method of claim 19, further comprising performing at least a portion of the procedure with the second guide catheter.

* * * * *